United States Patent [19]

Shapiro

[11] Patent Number: 4,641,648
[45] Date of Patent: Feb. 10, 1987

[54] SURGICAL INSTRUMENT
[76] Inventor: Marshall Shapiro, 7180 Pebblecreek, West Bloomfield, Mich. 48033
[21] Appl. No.: 781,028
[22] Filed: Sep. 27, 1985
[51] Int. Cl.⁴ .......................... A61F 1/24; A61B 17/00
[52] U.S. Cl. ..................................... 128/303 R; 623/7
[58] Field of Search ................... 128/303 R; 623/8, 7; 30/141, 324

[56] References Cited
U.S. PATENT DOCUMENTS

| | | | |
|---|---|---|---|
| 2,184,857 | 12/1939 | Dorozinski | 30/141 |
| 2,688,243 | 9/1954 | Bowen | 30/141 |
| 2,795,043 | 6/1957 | Fleischer | 30/141 |
| 3,456,301 | 7/1969 | Morroni | 30/324 |
| 3,727,306 | 4/1973 | Patik | 30/324 |
| 4,035,850 | 7/1977 | Cresswall | 128/303 R |
| 4,192,360 | 3/1980 | Rodriquez | 30/141 |

FOREIGN PATENT DOCUMENTS 280925  12/1914  Fed. Rep. of Germany ........ 30/141

Primary Examiner—Gene Mancene
Assistant Examiner—David I. Tarnoff
Attorney, Agent, or Firm—Krass & Young

[57] ABSTRACT

A surgical instrument and method for use in inserting and positioning prosthesis, including a body portion having an elongate hollow handle defining a feed trough for supplying normal saline solution to the body portion to aid in the insertion and positioning of a prosthetic implant.

1 Claim, 4 Drawing Figures

SURGICAL INSTRUMENT

TECHNICAL FIELD

This invention relates generally to surgical instruments and more particularly to a method and apparatus for surgically implanting and positioning mammary prostheses.

BACKGROUND OF THE INVENTION

One technique often utilized in cosmetic and reconstructive surgery is the implantation of a prosthesis into a particular body cavity in order to supplement or replace soft tissue in that area. In particular, the use of a polyurethane envelope filled with a silicone gel as mammary prosthesis has met with widespread success. The procedure for implanting a prosthesis typically involves making an incision in the desired area and implanting and positioning the prosthesis beneath the surface of the skin.

One of the desirable qualities of soft tissue implants is that the envelope which covers the implant material has a relatively high coefficient of friction. This helps to ensure that only minimal repositioning of the implant will occur after the implant is installed underneath the skin. However, the rough surface of the envelope can cause considerable problems during the initial installation and positioning of the implant.

There are a number of surgical instruments, such as forceps and skin retractors, which are employed in most surgical procedures involving plastic surgery. However, these tools have proven inadequate in procedures involving the implantation and positioning of prostheses having envelopes with high coefficients of friction relative to human tissue because any contact of the prosthesis with human tissue inhibits movement and positioning of the prosthesis.

SUMMARY OF THE INVENTION

In accordance with the present invention, the instrument includes a body portion having an elongate hollow handle. The body portion is of sufficiently large size and shape to cover a substantial portion of the implant surface. In operation, the implant is placed on top of the body portion covered with a polyethylene sleeve, and saline is poured down the hollow handle to reduce the frictional forces and aid in the insertion, positioning and removal of the body portion from the body cavity.

In the preferred embodiment, the instrument is provided as a part of a sterilized kit which includes the surgical instrument, with the implant positioned on top of the body portion and a polyethylene sleeve which covers the instrument and implant to ensure that the implant and instrument remain sterile. Since the instrument may be made of an inexpensive plastic material, the instrument and the polyethylene sleeve may be disposed of immediately following insertion of the implant.

DETAILED DESCRIPTION OF THE PREFERRED EMBODIMENT

Figure 1:
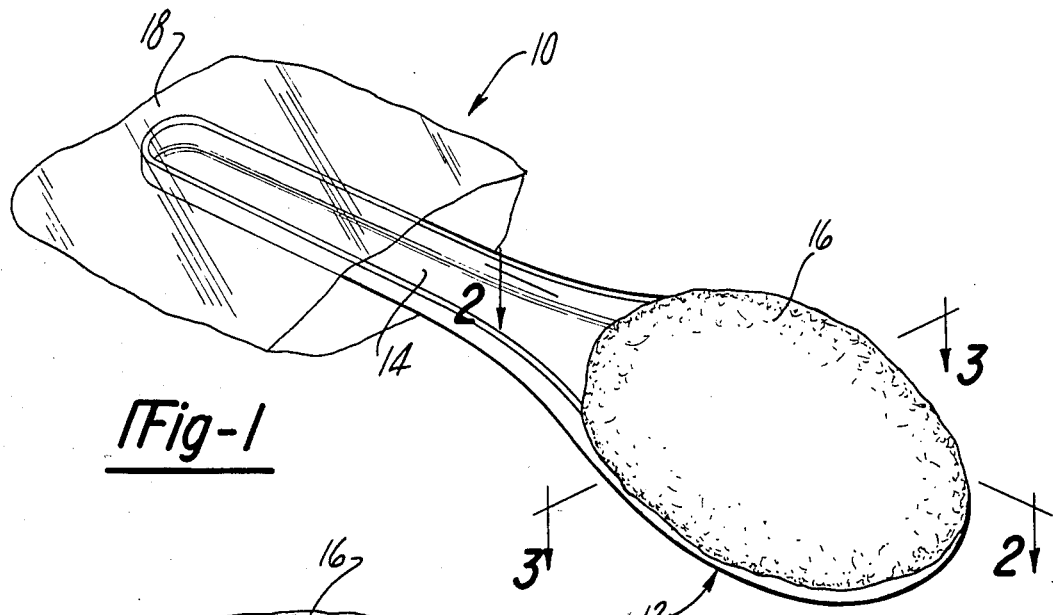
FIG. 1 is a prospective view of a surgical instrument embodying the features of this invention.

Referring to FIG. 1, the surgical instrument of the present invention, generally designated by the numeral 10, includes a body portion 12 having an elongate hollow handle 14. The body portion 12 is of a sufficient size and shape to cover a substantial surface area of the implant 16 when the implant 16 is placed on top of the body portion.

The elongated hollow handle 14 forms a conduit and allows for the flow of normal saline solution to the body portion 12 to reduce frictional forces during the insertion, positioning and removal of the implant 16.

Figure 2:
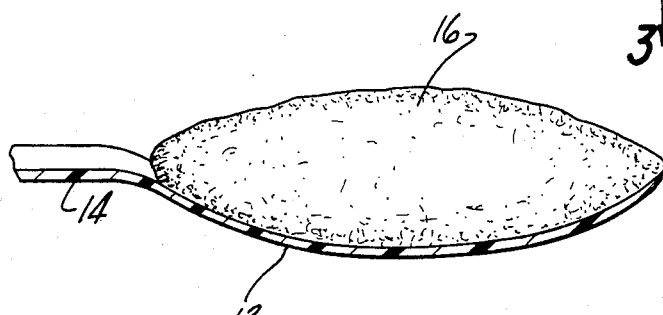
FIG. 2 is a side cross-sectional view taken along line 2 of FIG. 1.

Referring to FIG. 2, the inner surface of the body portion 12 is relatively smooth and preferably has a concave shape. The saline solution poured down the elongate hollow handle 14 allows the body portion 12 to be slidably withdrawn from the body cavity without moving the implant from its intended position.

Figure 3:
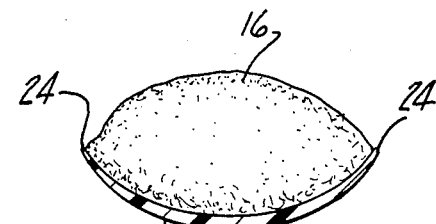
FIG. 3 is an end cross-sectional view taken along line 3 of FIG. 1.

Referring to FIG. 3, the cross section of the body portion 12 becomes progressively smaller from the center 22 to each of the edges 24. Thus, while the handle 14 and the center 22 of the body portion 12 is thick enough to provide rigidity and control during insertion of the implant 16, the eges 24 of the body portion 12 are thin enough so that pressure from each of the sides 24 will cause the body portion 12 and therefore the implant 16 contained thereon, to assume a shape closer to a tube.

Figure 4:
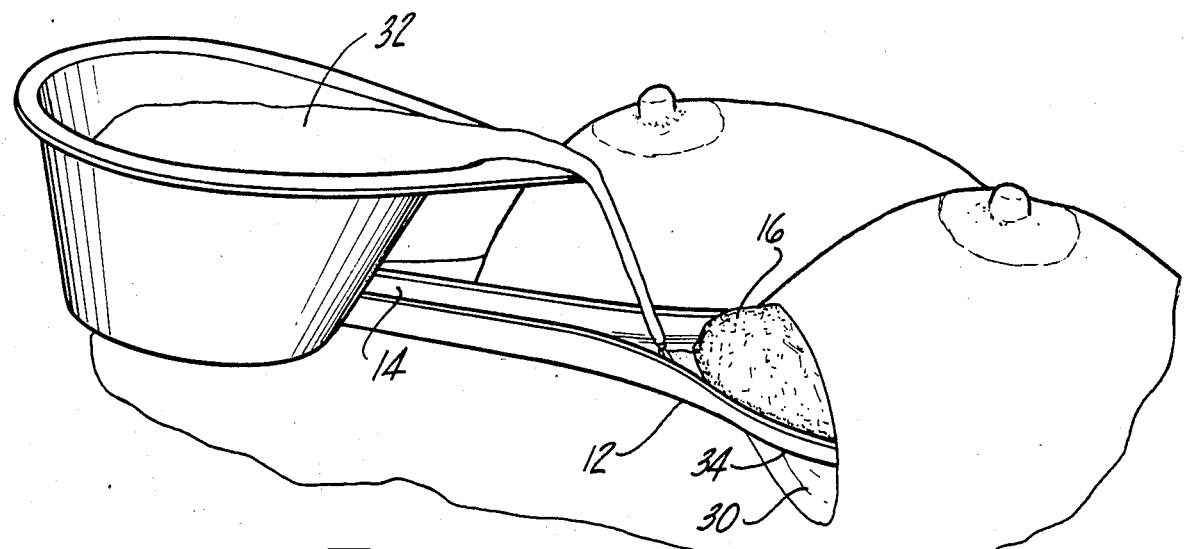
FIG. 4 is a prospective view of a mammary prosthesis being inserted in a human breast.

Referring to FIG. 4, the implant 16 is positioned on top of the body portion 12 of the tool and then inserted and positioned in the body cavity 30 of the patient. As previously described, saline solution 32 is poured down the handle 14. The body portion 12 of the surgical tool is then slidably removed from the body cavity 30 leaving the implant 16 in place. The frictional force caused by the now exposed surface of the implant 16 with the tissue 34 surrounding the body cavity 30, inhibits movement of the implant 16 and allows for subsequent removal of the surgical instrument. The surgical instrument 10 of the present invention is preferably made of a material such as plastic which provides the necessary combination of rigidity and flexibility for this surgical application.

It will be appreciated by those skilled in the art that several other structural features of the surgical instrument 10 facilitate easy removal of the instrument after the implant has been inserted into the desired position in the body cavity. In particular, the smooth concave surface of the body portion 12 in conjunction with the saline solution which may be applied through the elongate hollow handle 14, minimizes frictional forces between body tissue 34 and the outer surface of the body portion 12.

Referring to FIG. 1, the instrument is preferably one component of a kit which includes the instrument 10, the implant 16 and an antiseptic envelope 18, in which the instrument 10 and the implant 16 are hermetically sealed. In this manner, the surgical tool and implant may be sterilized, packaged and transported to the site of the surgery for immediate use. The implant 16 and tool 10 may then be removed from the antiseptic envelope 18, the surgery performed, and the envelope discarded. As will be appreciated by those skilled in the art, the inclusion of a disposable tool and a sterilized kit including the kit is convenient for the surgeon and helps to ensure that each patient enjoys sterile conditions during the surgical procedure. Thus, the present invention provides a safe, inexpensive means for facilitating the successful implantation of a mammary prosthesis.

I claim:

1. A method of inserting a prosthetic breast implant into a body cavity, which comprises:
   (A) guiding the prosthetic implant into the body cavity with a substantially spoon-shaped surgical instrument having an elongate, trough-shaped handle opening into a wider, concave implant-holding spoon portion wherein the implant is placed in said spoon portion;
   (B) applying normal saline solution through the handle of the surgical instrument to reduce the frictional forces between the implant, the surgical instrument and human tissue;
   (C) replacement and positioning of the implant within the body cavity using the surgical instrument; and
   (D) withdrawing the surgical instrument from the body cavity while leaving the prosthetic implant within the body cavity.

* * * * *